(12) United States Patent
Greiner-Perth (10) Patent No.: US 6,382,465 B1
(45) Date of Patent: May 7, 2002

(54) DISPENSER FOR THE OPTIONALLY ATOMIZED DISCHARGE OF AN IN PARTICULAR LIQUID MEDIUM FROM A CONTAINER

(75) Inventor: Juergen Greiner-Perth, Gottmadingen (DE)

(73) Assignee: Ing. Ercih Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/652,088

(22) Filed: Aug. 31, 2000

(30) Foreign Application Priority Data

Sep. 15, 1999 (DE) .......................................... 199 44 209

(51) Int. Cl.⁷ ................................................. B67D 5/00
(52) U.S. Cl. ......................... 222/82; 222/309; 222/326; 604/208
(58) Field of Search ........................... 222/82, 162, 320, 222/326, 309, 282, 386.5, 83, 325, 83.5; D24/114; 604/208, 211

(56) References Cited

U.S. PATENT DOCUMENTS

| 1,393,720 | A | * | 10/1921 | Lomas et al. ............. 12/142 N |
| 2,581,182 | A | * | 1/1952 | Fields ......................... 222/162 |
| 4,175,704 | A | * | 11/1979 | Cohen ......................... 222/320 |
| 4,475,905 | A | * | 10/1984 | Himmelstrup ............... 604/208 |
| 4,921,142 | A | * | 5/1990 | Graf et al. ................... 222/162 |
| 4,962,868 | A | * | 10/1990 | Borchard ............... 128/200.14 |
| 5,232,457 | A | * | 8/1993 | Grim ........................... 604/195 |
| 5,257,726 | A | * | 11/1993 | Graf et al. ................... 222/320 |
| 5,277,334 | A |   | 1/1994 | Malinconico |
| 5,284,132 | A | * | 2/1994 | Geier ..................... 128/200.22 |
| 5,289,818 | A | * | 3/1994 | Citterio et al. .............. 222/320 |
| 5,307,953 | A | * | 5/1994 | Regan .......................... 222/82 |
| 5,318,544 | A | * | 6/1994 | Drypen et al. ................. 604/2 |
| 5,427,280 | A |   | 6/1995 | Fuchs |
| D446,578  | S | * | 8/2001 | Jansen et al. ............... D24/110 |
| 6,321,942 | B1| * | 11/2001 | Krampen et al. ...... 222/153.05 |

FOREIGN PATENT DOCUMENTS

| DE | 37 05 352 A1 | 8/1987 |
| DE | 40 08 068 A1 | 9/1991 |
| DE | 197 00 437 A1 | 7/1997 |
| EP | 0 334 349 A1 | 9/1989 |
| EP | 0 373 963 A2 | 6/1990 |
| EP | 0 452 728 A1 | 10/1991 |
| EP | 0 477 562 A2 | 4/1992 |
| GB | 2 316 451 A  | 2/1998 |
| WO | WO 98/30335  | 7/1998 |

\* cited by examiner

Primary Examiner—Joseph A. Kaufman
Assistant Examiner—Stephanie L. Willatt
(74) Attorney, Agent, or Firm—Quarles & Brady LLP (57) ABSTRACT

A method of producing a flexible conduit whose dimensions and shape can easily be changed according to its use is described. The method includes producing elongate elements from an elastic flexible material, wherein the cross-section of the elongate elements each have at least one corrugation and extend so as to be rectilinear longitudinally. Each elongate element is fixed to at least one elongate holding element made of rigid pliable material so as to keep its shape after bending. Several sets of elongate elements are produced and are connected to each other along their adjacent longitudinal edges in order to form a flat enclosure whose dimensions correspond to those of the deployed flexible conduit. The flat enclosure is then deformed so as to close it and to obtain the required shape of the cross-section of the conduit, wherein the enclosure is kept in shape by the deformation of the elongate holding elements. Then, the adjacent ends of the shaped enclosure are connected.

20 Claims, 6 Drawing Sheets

DISPENSER FOR THE OPTIONALLY ATOMIZED DISCHARGE OF AN IN PARTICULAR LIQUID MEDIUM FROM A CONTAINER

FIELD OF APPLICATION AND PRIOR ART

The invention relates to dispensers for the optionally atomized discharge of an in particular liquid medium from a container.

Such a dispenser is e.g. known from EP 334 349 A1, in which the medium is discharged by the manual operation of an operating member. The operation is subdivided into a sequence of partial operations and during each partial operation a clearly defined partial charge of the medium is discharged. In order to prevent that two successive partial operations are performed in uninterrupted succession, it is known from the aforementioned document that a changeover operation is required between two partial operations of the operating member.

Such dispensers are in particular used if a medicament or a vaccine is to be applied to the nasal mucosa of a patient. An atomized discharge of the medium has the advantage that the active ingredient is more easily absorbed by the patient. One example in which the dispenser is also suitable for use by the patient consists of anti-migraine agents to be applied to the nasal mucosa.

The medium must conventionally be discharged in two and optionally a small number of partial charges having a clearly defined and usually identical size from the dispenser. In the interest of maximum use reliability it is proposed that the operating path of the operating member is deliberately interrupted, to ensure that in a continuous operation of the operating member no more than one partial charge is discharged at once as a result of an oversight.

To ensure this a changeover operation is necessary between the partial operations of the operating member.

However, the performance of such a changeover operation requires a setting down of the dispenser from the application point and is prejudicial to a one-handed operation of the dispenser.

However, such a one-handed operation of such a dispenser is particularly desirable if the user needs the second hand for fixing the discharge point, e.g. for fixing the head of a patient, particularly a child and which is consequently unavailable for dispenser operation. A setting down of the dispenser and a release of the fixing of the application point for performing the changeover operation and a subsequent refixing of the application point and a reattachment of the dispenser would be very cumbersome.

PROBLEM AND SOLUTION

Thus, the problem of the invention is to so further develop such a dispenser that a one-handed operation is possible, where it is ensured that a discharge of more than one partial charge in a single operation is reliably prevented.

In the case of a dispenser of the aforementioned type, this problem is solved by the characterizing features of claim 1 of the present invention. In the case of a dispenser according to the invention for the optionally atomized discharge of an in particular liquid medium from a container, dispenser operation takes place in a sequence of manual partial operations of an operating member. During each of the partial operations of the operating member a clearly defined partial charge is discharged from the dispenser. A changeover or reversing operation takes place between two partial operations of the operating member. This changeover operation takes place automatically following the performance of a partial operation.

According to advantageous developments of the invention for the performance of the changeover operation force reservoirs or accumulators are provided, which are pretensioned during the performance of a partial operation. These force reservoirs can be simultaneously used to ensure that the operating member is returned from an operating end position reached when a partial operation has been completely performed into the operating starting position and the following partial operation can be performed from the operating starting position. It is particularly advantageous to perform the changeover operation when the end of the partial operation is established in that the operating force necessary for performing the partial operation no longer acts on the operating member.

According to a development of the invention the force reservoir can be constituted by springs, particularly spiral springs.

According to further developments of the invention the container is placed in a casing and between the casing and the operating member a relative movement takes place during each partial operation, said relative movement being fixed by a connecting link guide. Connecting link guidance in particular takes place through a connecting link path in which a sliding block is guided. According to a preferred embodiment between the casing and the container is provided a sleeve, which is either stable to the casing or the container with respect to a partial operation of the operating member, but is relatively movable in the direction of the changeover operation. The sleeve either has the connecting link path or the sliding block guided in said path. Further preferred developments of the connecting link guide are given in the further subclaims, which in particular relate to the design of the connecting link path and the construction of the force reservoirs on said path.

Besides being illustrated by the subclaims, the invention is further illustrated by the embodiment shown in the attached drawings, wherein show:

FIGS. 3a/3b to In each case cross-sectional representations and part

FIGS. 6a/6b sectional representation of a second embodiment in which the sleeve is stable with respect to the container during different positions arising during the sequence of partial operations of the dispenser.

Figure 1:
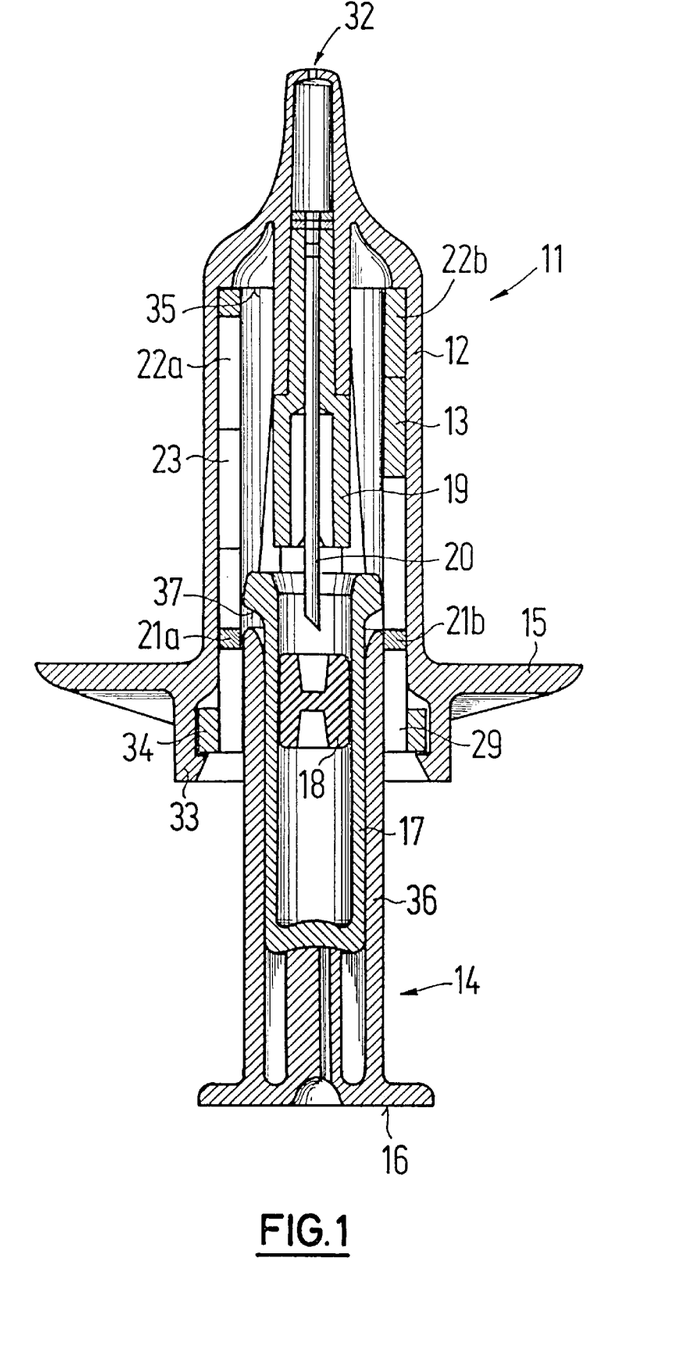
FIG. 1 A sectional view through a first dispenser according to the invention, in which a sleeve with a connecting link path is arranged in stable manner with respect to a casing receiving the container.
Figure 2A:
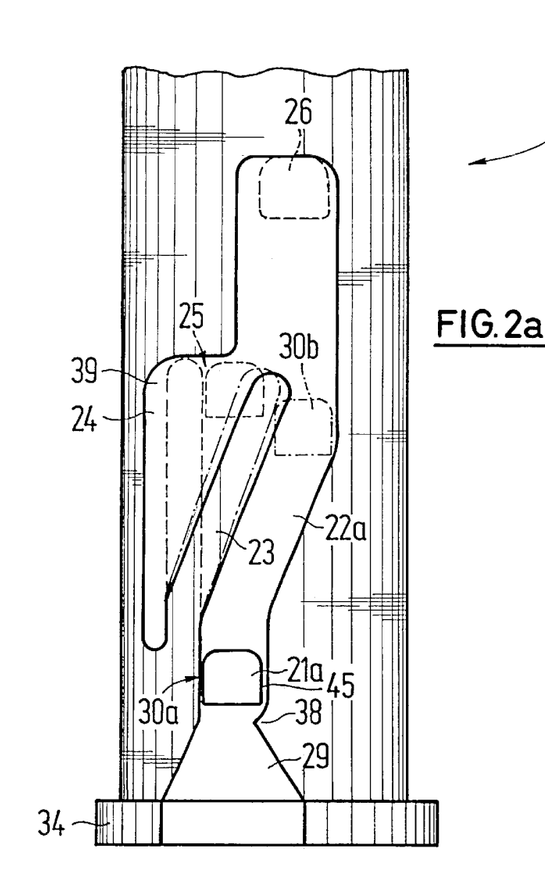
FIGS. 2a & 2b Side views of a sleeve for use in the embodiment according to FIG. 1.
Figure 2B:
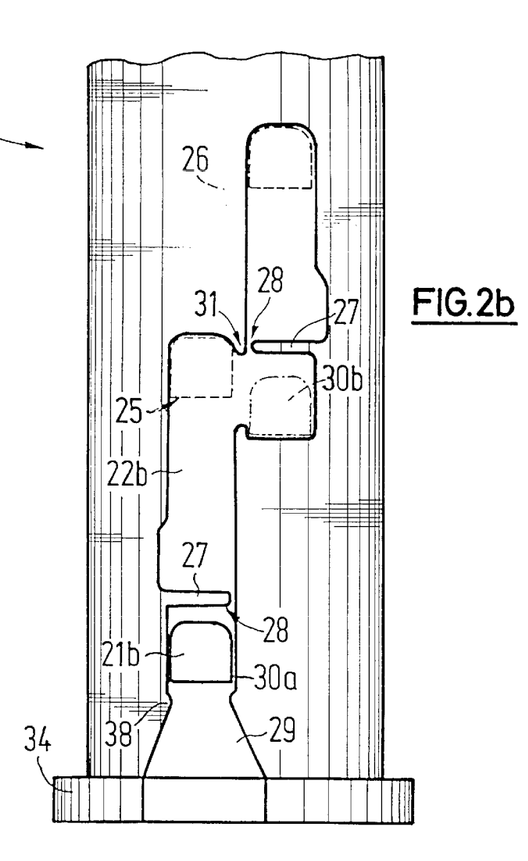

DESCRIPTION OF THE EMBODIMENT ACCORDING TO FIGS. 1 TO 2B

FIG. 1 shows in cross-sectional form a dispenser according to the invention having a thrust piston construction. The dispenser 11 comprises a casing 12, the sleeve 13 held in rotary manner in said casing, the operating member 14, which simultaneously serves as a receptacle for the ampoule 17, which constitutes a container for the medium to be discharged. The ampoule 17 is sealed by the plug 18 prior to the first operation. The ampoule 17 is so held in the operating member 14 that on operating the operating member in the direction of the casing it is moved together with said operating member. During the first operating partial stroke the plug 18 is firstly perforated by the cannula 20, which forms a discharge channel up to the nozzle 32. The plug 18, which then serves as a piston, is then pressed into the ampoule by the piston rod 19 located in the casing 12, so that the ampoule volume available for the medium is reduced. The medium escapes via the cannula 20 and nozzle 32 and is in this way discharged. As a result of the subdivision of the operating path in the present case into two partial operations, during each of said two partial operations the plug 18 is only pressed into the ampoule by a predetermined amount and in the present case by half the total possible operating path.

At its front end the casing 12 of dispenser 11 has the nozzle 32, whilst at its rear end it has the finger support 18 for supporting at least one finger. The finger support 15 is used for the application of a force to the casing assisting the operating force acting on the operating member 14, so that the dispenser is kept still during operation. The sleeve 13 is arranged along the wall of the casing. In the axial operating direction of the operating member 14 the sleeve 13 is supported on the support edge 35 of the casing 12. At its rear end the sleeve 13 has an edge 34, behind which engages the casing-side locking edge 33 in such a way that the sleeve 13 cannot be drawn rearwards out of the casing 12. Thus, the support edge 35 and locking edge 33 form a mounting support for the sleeve 13 in the casing defining in the operating direction of the operating member 14 a stable mounting of the sleeve 13 in the casing 12. The sleeve 13 can be rotated in the casing 12 about a rotation axis running in the operating direction of the operating member 14. At its rear end the operating member 14 has an operating face 16, which is used for the manual operation of the operating member 14, particularly by means of the thumb of the user. Otherwise the operating member 14 is essentially formed by the hollow cylindrical shaft 36. The hollow cylindrical shaft 36 has an external diameter essentially corresponding to the internal diameter of the sleeve 13. The shaft 36 is guided in the casing 12 by the sleeve 13. For the construction of a connecting link guide the sleeve 13 has on each of the facing sides a connecting link path, as is shown in greater detail in FIGS. 2a and 2b. Sliding blocks 21a, 21b are formed at corresponding points in the vicinity of the front end of the shaft 36 of the operating member 14. The ampoule 17 with the medium stored therein is inserted in the shaft 36. The internal diameter of the shaft essentially corresponds to the external diameter of the ampoule, so that there is a clamping mounting of the ampoule 17 in the shaft 36 of the operating member 14. At its front end the ampoule also has a cross-sectional widening, which as an abutting edge 37 can engage with the leading edge of the shaft 36 ensuring that during the operation of the operating member 14 the ampoule 17 is carried along in zero-backlash manner in its operating direction.

FIGS. 2a and 2b show opposite side views of the sleeve 13 with the connecting link paths 22a, 22b and the sliding blocks 21a, 21b in each case guided in the connecting link path. The connecting link path 22a shown in FIG. 2a is used for pretensioning a force reservoir for performing the changeover operation between the two partial operations of the operating member, whereas the connecting link path shown in FIG. 2b is used for subdividing the operating path of the operating member into two partial operations.

In the vicinity of the sleeve edge 34 each of the two connecting link paths has an introduction funnel 29 for the easy introduction of the sliding blocks 21a, 21b into the particular connecting link path 22a, 22b. In addition, pressure point means 38 are constructed in the end region of the introduction funnel 29 so as to prevent a sliding of the sliding blocks 21a, 21b rearwards out of the connecting link path 22a or 22b. This prevents the loss of the operating member 14.

The connecting link path shown in FIG. 2a has a spring arm 23, which projects into the movement space of the sliding block 21a and is pressed by the latter during the first partial operation, accompanied by the production of a pretension, into the material-free displacement space 39 in the vicinity of the sleeve. The spring arm 23 is preferably made from the same material as the sleeve and can be constructed as a thin material web in the material-free area of the connecting link path 22a. The sleeve 13 is preferably made from plastic and the spring arm 23 can be produced in the same injection moulding process as the sleeve 13.

The displacement of the spring arm 23 from the movement space of the sliding block 21a is necessary because the path curve of the second connecting link path 22a located in the opposite position on the sleeve in FIG. 2b passes linearly over the entire length of a first partial operation. This prevents the sliding block 21a, guided by the spring arm 23, producing at this time a rotary movement of the sleeve 13 in the casing 12.

FIG. 2a shows an advantageous embodiment of the sliding block 21a. It is only rounded on its front side so as to avoid a spreading in the connecting link path 22a. It also has at least one flank 45 which, as a result of its longitudinal extension parallel to the linear path portions of the connecting link path, ensures a long guidance of the sliding block 21a in the connecting link path 22a. The sliding block 21b shown in FIG. 2b can also have a corresponding shape with a flank 45.

As can be gathered from FIG. 2b the sliding block 21b is guided in a connecting link path 22b comprising two linear path portions, which are mutually displaced by approximately the width of the connecting link path, the length of the two linear portions in each case corresponding to the operating path of a partial operation of the operating member 14. The two linear portions overlap in an area of this length roughly corresponding to the diameter of the sliding block 21b. On operating the operating member 14 with respect to the sliding blocks 21a, 21b, initially the sliding block 21b runs on the blocking means 27, namely a thin material web projecting on one side of the connecting link path 22b and which is connected by means of a predetermined breaking point 28 with the opposite edge of the connecting link path 22b and following separation at the said breaking point can be entirely removed from the connecting link path. Only if application takes place to the operating member 14 of an operating force leading to the breaking at the predetermined breaking point 28, is the material web forming the blocking means 27 pressed laterally out of the connecting link path 22b. Thus, the blocking means 27 with its predetermined breaking point 28 ensures that such an operating force is applied to the operating member 14 that there is a complete partial operation of the operating member in a continuous operating sequence. The sliding block 21b then slides in a linear, uninterrupted movement up to the end of the first partial operating end position 25 formed at the end of the first linear portion of the connecting link path 22b. In this position the sliding block 21a shown in FIG. 2a is in the vicinity of the front end of the spring arm 23 which, in the represented example, has been forced out to the left from the movement space of the sliding block 21a and now presses against the same with a corresponding unsupported length and the force produced as a result of material deformation against the sliding block 21a.

If the operating member 14 is not rotatable to the casing 12—here the retarding action resulting through the cannula 20 located in the plug 18 and the piston rod 19 of the casing 12 engaging on the plug and optionally also on the inside of the ampoule can be too great—the sleeve 13 is rotated with respect to the operating member 14 with the sliding blocks 21a, 21b formed thereon as a result of the force produced in the spring arm 23. This is only possible in the overlap area of the two linear portions of the connecting link path 22b. In order to achieve a clean separation between the two partial operations, on the area of the first linear portion of the connecting link path 22b corresponding to the first partial operation end position 25 is formed a relief nose 31, which prevents a rotation of the sleeve 13 with respect to the sliding blocks 21a, 21b for as long as the operating member 14 has not been completely relieved of the operating force. Only then can the relief nose be overcome and the sleeve can be moved in the operating direction of the operating member 14. Through the rotation of the sleeve with respect to the sliding blocks 21a, 21b and the casing 12 holding the sleeve 13, the sliding block 21b reaches the operating starting position 30b. As a result of a further operation of the operating member 14 the sliding block 21b initially again engages on the blocking means 27 with a predetermined breaking point 28, which has to be overcome with a minimal operating force on the operating member. The movement space for the second partial operation, formed by the second linear portion of the path curve of the connecting link path 22b is then freed. As shown in FIG. 2a, the connecting link path 21a is constructed in such a way that both the rotary movement and also the partial operating movement through the sliding block 21a is freed within the path curve of the connecting link path 22a.

A return preventing the retraction of the operating member 14 at the end of the partial operations is achieved by the path curve of the connecting link path 22a shown in FIG. 2a in conjunction with the spring arm 23 and the shaping of the sliding block 21a in that the sliding block, during the retraction of the operating member, is moved by means of the spring arm 23 into the dead shaft 24 as soon as the changeover operation has been performed by the spring arm 23.

It is alternatively possible to place the sleeve 13 in non-rotary manner in casing 12. It must then be ensured that the retarding effect, particularly between plug 18 and cannula 20, is not so large that a rotation of the ampoule 17 with operating member 14 in sleeve 13 is not prevented as a result of the force produced by the spring arm 23. Such a design has the advantage that in particular in the case of an operating face 16 made rough by ribbing, a rotation of ampoule 17 and operating member 14 is only possible if the user releases the operating member. This also reliably prevents two partial operations being successively performed without any interruption.

Figures 3A, 3B:
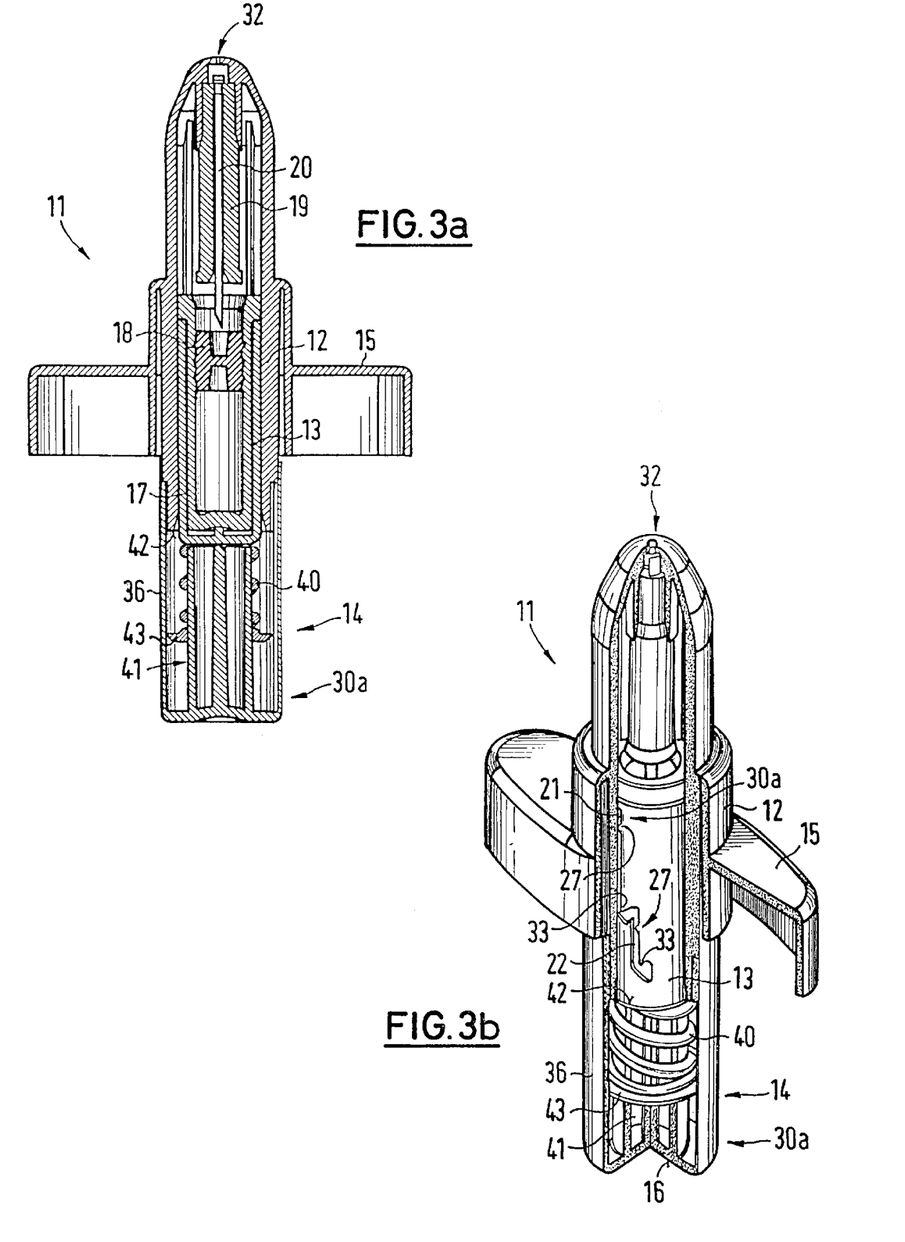

DESCRIPTION OF THE EMBODIMENT ACCORDING TO FIGS. 3a/3b TO 6a/6b

Figure 6A:
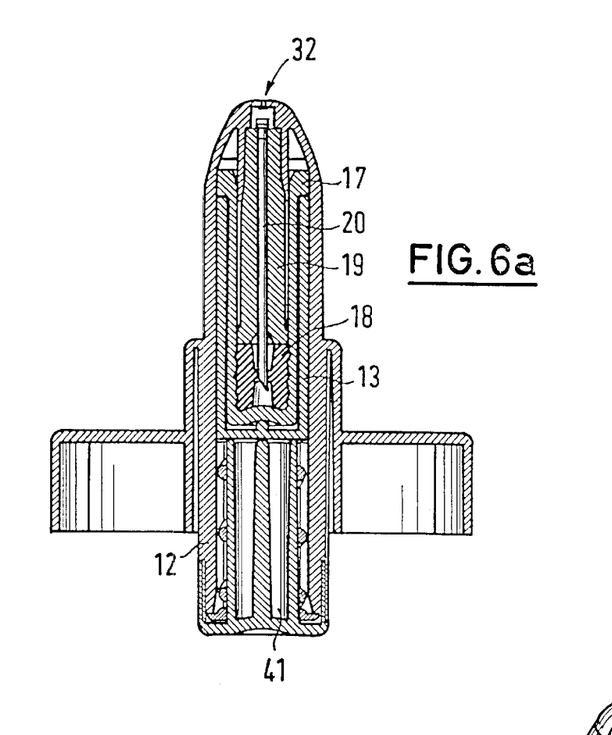

FIGS. 3a/3b to FIGS. 6a/6b in each case show in sectional representation and part sectional perspective view the different operating positions of a dispenser according to the invention, in which the partial operations of the operating member are produced by means of a connecting link guide, which uses a sleeve which, in the operating direction of the operating member, is stable with respect to the container for the medium to be discharged.

FIGS. 3a and 3b show the situation prior to the first operation of the dispenser 11. The dispenser 11 comprises a casing 12 with the finger support 15 constructed thereon. The ampoule 17 is held in the casing 12 in which is guided the sleeve 13. The ampoule 17 is sealed by the plug 18. The medium is discharged from the ampoule 17 in that during the initial operation the cannula 20 perforates the plug 18 and subsequently the plug 18, acting as a piston, is displaced synchronously with the cannula 20 in relative manner with respect to the ampoule 10, so that the medium volume in the ampoule is reduced. The plug 18 is subject to the action of the piston rod 19 as soon as the cannula 20 has perforated the plug 18. The medium then passes out of the ampoule through the discharge channel formed by the cannula 20 and reaches the nozzle 32 in casing 12, where the medium is atomized and discharged from the dispenser. The operating member 14 comprises a hollow cylindrical sleeve formed by the shaft 36 and by an operating face 16, which is located at the rear end of the operating member 14 remote from the nozzle 32. The shaft 36 of the operating member is axially displaceably mounted in the casing 12. The sleeve 13 has the connecting link path 22 of the connecting link guide in which engages the sliding block 21 constructed on the casing 12.

The sleeve 13 with the ampoule 17 held therein is held in guided manner in the casing 12 and projects rearwards into the shaft 36 of the operating member 14. At the rear end of the sleeve 13 is located the spiral spring 40 as the force reservoir for performing the changeover operation.

The spiral spring shown in FIG. 3 is constructed in such a way that the spring is only pretensioned when the operating member has already covered part of the partial operating path. This in particular reduces the minimum operating force which has to be applied so as to ensure that each partial operating stroke is uninterruptedly discharged as a complete stroke.

The spiral spring 40 is not only used for performing the changeover operation, but also for the transfer of the operating member 14 from its operating end position reached at the end of an operation into the operating starting position of the following partial operation.

The connecting link path 22 of the connecting link guide constructed on the sleeve 13 comprises two axially directed, radially mutually displaced partial portions, which in each case define the operating path of a partial operation and an inclined path portion passing between said two portions and defining the changeover operation between the two partial operations. At the start of each of the two axially oriented portions defining the partial operations is provided a blocking means 27 defining the operating starting positions 30a, 30b in the form of a locking nose, which projects into the path. The blocking means are constructed in such a way that they can press over on exceeding a minimum operating force on operating member 14. At the rear end of the first axial portion of the path curve of the connecting link path 22 defining the partial operation is formed a locking edge 33, which can be travelled over in the operating direction by the sliding block 21 guided in the connecting link path 22, but which in the opposite direction ensures that the sliding block 21 does not pass back into the axial portion of the first partial operation and instead blocking in this direction moves the sliding block along the connecting portion defining the changeover operation.

Figure 4A:
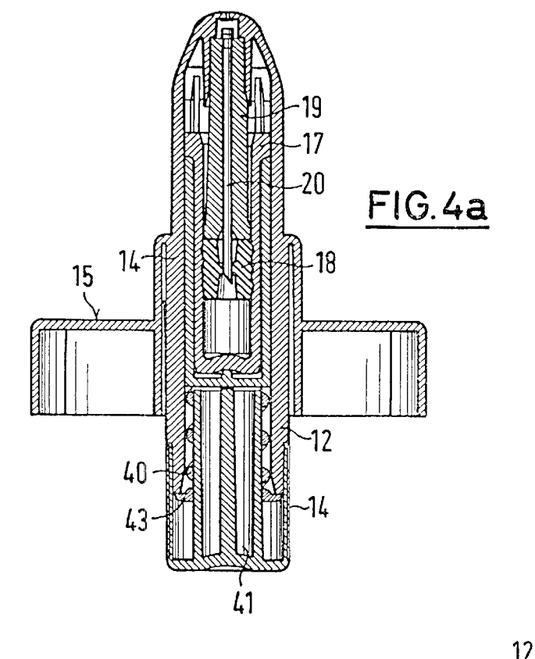
Figure 4B:
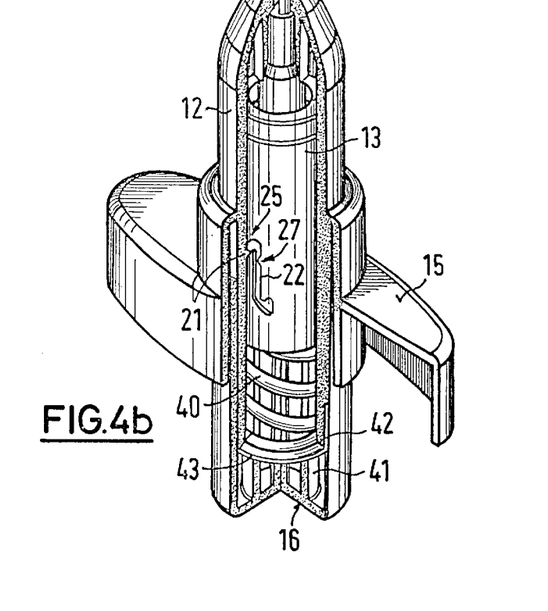

FIGS. 3a and 3b show the starting position prior to the initial dispenser operation. The casing-side sliding block 21 is in the operating starting position 30a at the start of the first axially directed path curve portion of the connecting link path 22 defining the first partial operation. This position is defined by means of the blocking means 27 and can only be transferred into the operating end position by overcoming a minimum operating force ensuring a continuous, uninterrupted operation into the first partial operating end position, as shown in FIGS. 4a and 4b. If the operating member 14 is operated on its operating face with more than the necessary minimum force, a corresponding counterforce being introduceable by means of the finger support on the casing, the resistance of the blocking means 37 is overcome and the sliding block 21 slides in a linearly directed movement along the corresponding portion of the connecting link path 22 of the sleeve 13. This takes place because the operating member 14 is moved relative to the casing 12 in the direction of the nozzle 32, the ram 41, which is formed within the shaft 36 of the operating member 14, acting on the sleeve or the ampoule located in said sleeve with a force, so that the sleeve and ampoule 17 are moved forwards in the direction of the cannula 20 in the casing. The cannula 20 perforates the plug 18 and then the piston rod 19 engages on the plug 18 and moves the latter rearwards in the ampoule 17, the medium volume being reduced, so that medium is discharged through the cannula 20 and atomized in the nozzle 32. During the last quarter of this first partial operation the spiral spring fixed on one side on the ram 41 engages on the casing underedge 42, so that on the spiral spring 40 is formed a driving ring 43. During the further movement of the ram with the operating member 14 relative to the casing 15, the spring is pretensioned. The movement continues until the sliding block 21 reaches the end of the linear portion corresponding to the first partial operation and shortly prior to reaching the first partial operating end position 25 constructed as a reversal point the locking edge 33 is overcome ensuring that the sliding block 21 no longer passes into the path curve portion corresponding to the first partial operation.

This situation is illustrated in FIGS. 4a and 4b, where the spring 40 is pretensioned. As a result of the locking edge 33, the sliding block 21 is forced into the transition portion constituting the connection between the two portions of the path curve of the connecting link 22 defining the partial operations. This transition portion passes substantially transversely, but slightly forwardly, the two axial portions defining the partial operations being mutually displaced by more than a width of the connecting link path. As a result of the already performed operation of the operating member 14 the plug 18 has been forced in the direction of the base of the ampoule 17 and on reaching the reversal point by the sliding block 21 in the connecting link path 22, reaches a clearly defined partial operating end position 25 corresponding to the discharge of a predefined medium quantity.

As soon as the operating face 16 is released and consequently no longer does any operating force act on the operating member 14, as a result of the pretension of spring 40 the changeover operation takes place, in which the sleeve 13 is rotated about a rotation axis relative to the ampoule 17 passing coaxially to the operating direction during the partial operations. If in alternative manner the sleeve is held in non-rotary manner with respect to the ampoule 17, the sleeve 13 with ampoule 17 and operating member 14 is rotated to the casing 12 as soon as the operating face 16 is released.

Figure 5A:
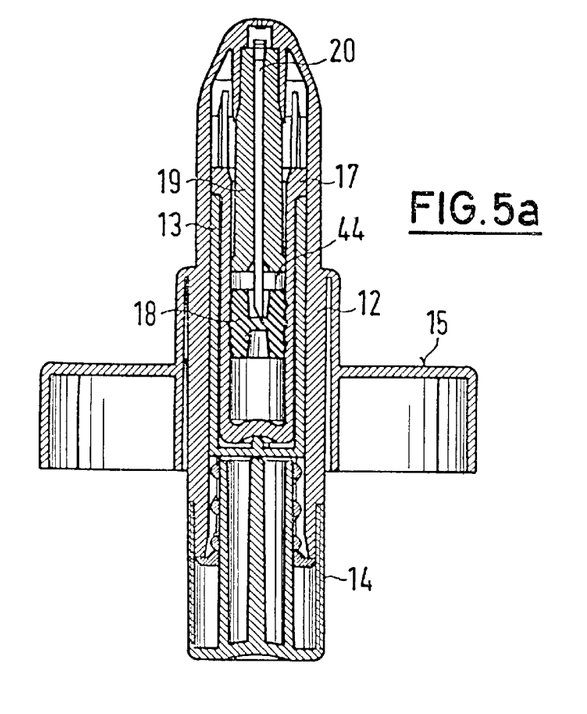
Figure 5B:
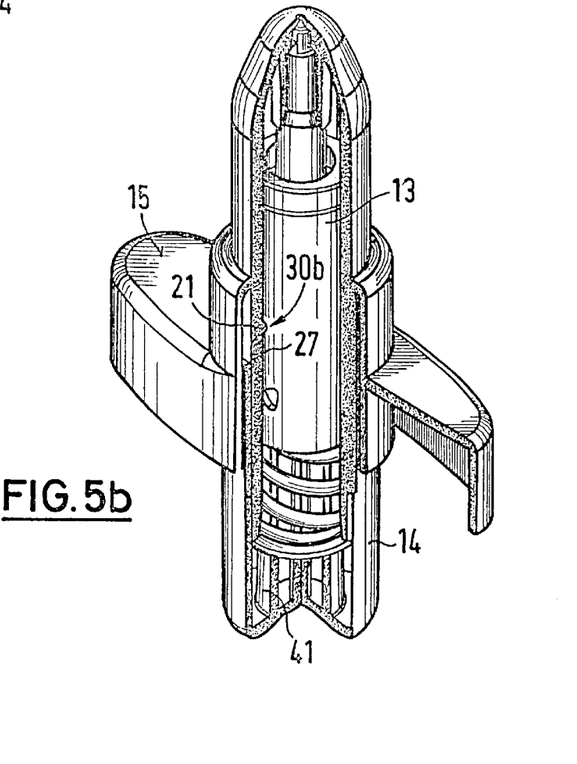

As a result of the slightly forwardly directed shape of the path curve simultaneously the sleeve 13 with the ampoule 17 fixed therein is retracted by a small amount in the casing 12, so that between the piston rod 19 and plug 18 a small gap 44 is formed and the cannula 20 is partially retracted from the plug 18. This position is shown in FIGS. 5a and 5b, which form the operating starting position prior to the second partial operation. The sliding block 21 is now in the operating starting position 30b directly in front of the blocking means 27, which ensures the minimum operating force for performing a continuous second and final partial operation until the operating end position is reached. The spiral spring 40 is, together with its driving ring 43, in engagement with the casing underedge 42. As a result of this fact, the second partial operation takes place entirely against the action of the spiral spring 40. Thus, a slightly increased operating force compared with the first partial operation is necessary for performing the second partial operation, which is compensated by the fact that the cannula 20 no longer has to completely perforate the plug.

Figure 6B:
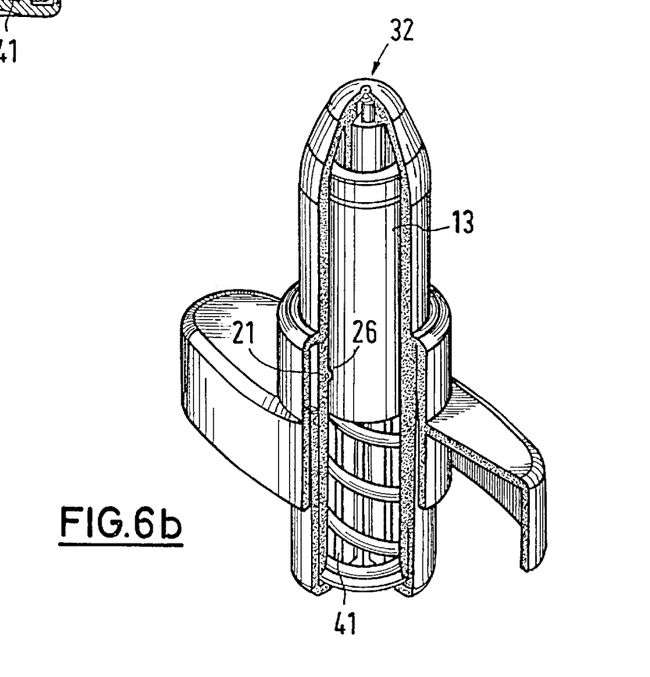

Following onto the operating starting position 30b extends the second, axially directed portion of the path curve of the connecting link path 22 of the connecting link guide. As soon as the operating member 14 again exceeds with an operating force the minimum amount defined by the blocking means 27, the sleeve 13 is moved further forwards. The cannula 20 again perforates the plug 18 which, after overcoming the idle path given by the gap 44, engages again on the piston rod 19. The plug 18 is then moved down to the base of the ampoule 17. The operating end position of the first and final partial operation of the dispenser shown in FIGS. 6a and 6b is reached accompanied by the discharge of the second partial charge, whose volume corresponds to the first partial charge. At the end of the partial operation the sliding block reaches the second partial operating end position 26 of the connecting link path 22. The latter is preferably constructed in such a way that the sliding block 21 is so held in this partial operating end position that the sliding block can be moved back by overcoming a catch into the connecting link path.

During the second partial operation there is also a force transfer from the operating member 14 to the sleeve 13 and the ampoule 17 by means of the operating member ram 41.

What is claimed is:

1. Dispenser for discharging medium from a container for discharge operation in at least two partial strokes performed in an operating direction, thereby discharging with each of the two partial strokes a partial charge of the medium, comprising:

a discharge opening for the medium connected to the pump by a discharge channel, an operating member for manually operating the pump by exerting a manual operation force, guiding means for the operating member, at least one path (22b) for the guiding means including first and second partial stroke paths, the first partial stroke path allowing operation of a first one of said two partial strokes, the guiding means being guided along said first partial stroke path and interrupting the operation at a first partial stroke end position occupied by the operating member after said first one of said two partial strokes, changeover means for automatically transferring said guiding means to said second partial stroke path allowing operation of the second one of said two partial strokes, the changeover means including at least one spring, said spring being loaded during said first partial stroke, at least one blocking means (27) being provided in each partial stroke path for preventing partial strokes of the operating member (14), before a predetermined level of said operating force is applied to the operating member (14) for performing one of said two partial strokes.

2. Dispenser according to claim 1, wherein the blocking means are projections (27) molded together with and projecting from a wall of the guide path.

3. Dispenser for discharging medium from a container for discharge operation in at least two partial strokes performed in an operating direction, thereby discharging with each of the strokes a partial charge of the medium, comprising:

a discharge opening for the medium connected to the pump by a discharge channel, an operating member for manually operating the pump by exerting a manual operation force, guiding means for the operating member, at least one guide path (22b) for the guiding means including first and second partial stroke paths, the first partial stroke path allowing operation of the first one of said two partial strokes while the guiding means being guided by said first partial stroke path and interrupting the operation at a first partial stroke end position occupied by the operating member after said first one of said two partial strokes, changeover means for automatically transferring said guiding means along a changeover path to said second partial stroke path allowing operation of the second one of said two partial strokes, the changeover means including at least one spring acting transversely to said operating direction, said spring being loaded during said first partial stroke.

4. Dispenser according to claim 3, wherein the spring is a blade spring made from plastic material.

5. Dispenser according to claim 3, wherein the blocking means are projections (27) molded from plastic material together with and projecting from a wall of the guide path.

6. Dispenser according to claim 3, wherein at least one blocking means (27) is provided in each partial path preventing partial operations of the operating member (14), before a predetermined level of said operating force is applied to the operating member (14) for performing the partial stroke.

7. Dispenser according to claim 3, further comprising preventing means (31) for preventing the changeover means from operating as long as the operating force necessary for performing the partial strokes acts on the operating member (14).

8. Dispenser according to claim 3, wherein the container (17) is placed in a casing (12) and between the casing (12) and the operating member (14) a relative movement takes place during each partial stroke, said relative movement being guided by guide paths being formed as sliding links.

9. Dispenser according to claim 8, wherein the sliding links comprise at least one sliding link path (22, 22a, 22b), in which a sliding member (21, 21a, 21b) is guided.

10. Dispenser according to claim 9, wherein a sleeve (13) is placed between the casing (12) and container (17), the sleeve (12) either having the connecting link paths (22, 22a, 22b) or the guiding means in form of a sliding block (21, 21a, 21b) guided therein, the sleeve being positioned in stable manner either with respect to the casing or the container (17).

11. Dispenser according to claim 10, wherein the sleeve (13), in the operating direction, is stable either respect to the casing (12) or the container (17) and is movable relative thereto in direction of the changeover operation.

12. Dispenser according to claim 10, wherein the sleeve (13) has at least one of said connecting link paths (22, 22a, 22b).

13. Dispenser according to claim 12, wherein the sleeve (13) is stable with respect to the housing (12) in the operating direction of the partial strokes of the operating member (14) and the sliding member (21, 21a, 21b) is constructed on the operating member (14).

14. Dispenser according to claim 12, wherein the sleeve is stable with respect to the container (17) in the operating direction of the two partial strokes and the sliding member (21, 21a, 21b) is constructed on the casing (12).

15. Dispenser according to claim 3, wherein the guide path (22b) and the changeover path each cooperate with a sliding member (21a, 21b), the guide path (21b) having a stepped path shape with the step interrupting the operation at the first partial stroke end position and the changeover path having a shape containing a movement space for the sliding member and a displacement space for a spring arm (23) which is slid transversely out of the movement during the first partial stroke and moves the sliding member transversely at the first partial stroke end position into a position for a following partial stroke.

16. Dispenser according to claim 15, wherein the spring arm (23) is constructed in such a way that it forms a retraction barrier for the sliding member (21a).

17. Dispenser according to claim 3, wherein the container is an ampoule (17) used as a cylinder of a thrust piston pump, which ampoule is sealed with a plug (18), the discharge opening (32) terminates at its side remote from the discharge opening in a cannula (20), which perforates the plug (18) during the first partial stroke, the plug (18) during each partial stroke is moved into the ampoule by a predetermined amount and a predetermined volume medium is displaced into the discharge channel.

18. Dispenser for discharging medium from a container for discharge operation in at least two partial strokes performed in an operating direction, thereby discharging with each of the two partial strokes a partial charge of the medium, comprising:

a discharge opening for the medium connected to the pump by a discharge channel, an operating member for manually operating the pump by exerting a manual operation force, guiding means for the operating member, at least one guide path (22b) including first and second partial stroke paths, the first partial stroke path allowing operation of the first one of said two partial strokes while the guiding means being guided by said first partial stroke path and interrupting the operation at a first partial stroke end position occupied by the operating member after said first one of said two partial strokes, changeover means for automatically transferring said guiding means to said second partial path allowing operation of a second one of said two partial strokes, the changeover means being situated in a changeover path including at least one spring being loaded during said first one of said two partial strokes.

19. Dispenser according to claim 18, wherein all the paths are in the form of slits for the guiding means, which are in the form of a path follower.

20. Dispenser for discharging medium from a container for discharge operation in at least two partial strokes performed in an operating direction thereby discharging with each of the two partial strokes a partial charge of the medium, comprising:

a discharge nozzle for the medium connected to the pump by a discharge channel, an operating member for manually operating the pump by exerting a manual operation force thereon, the operating member (14) being moveable into a casing (12) and having an operating surface (16) for a finger of the user, a finger support (15) at the casing (12) for operating the dispenser, a sleeve (13) having a guide slit (22b), in which a first sliding member (21b) is guided, and a changeover slit (22a), in a second sliding member (21, 21a, 21b) is guided, the guide slit having generally a Z-shape and having at least first and a second substantially linear slit sections parallel to the operating direction, and in each of said linear slit sections a blocking projection (27) is projecting from a wall of the slit (22b), each blocking projection preventing start of a partial stroke unless a predetermined level of the operating force is applied to the operating member, the first sliding member sliding, during the first one of the two partial strokes, in the first slit section, the guide slit having an intermediate section between both of the linear slit sections defining a rest shoulder for the first sliding member (21b) in a first partial stroke end position (25) for interrupting -the operation after the first one of the two partial strokes, the changeover slit (22a) containing a blade-like spring (23) being tensioned by the second sliding member (21a) during the first one of the two partial strokes, both paths and the sliding members being so arranged that after the first one of the two partial strokes the spring (23), acting on the second sliding member (21a), moves the first sliding member (21b) in the intermediate section into the second slit section in which it is in a start position (30b) for a second one of the two partial strokes.

\* \* \* \* \*

UNITED STATES PATENT AND TRADEMARK OFFICE
CERTIFICATE OF CORRECTION

PATENT NO.    : 6,382,465 B1
DATED         : May 7, 2002
INVENTOR(S)   : Juergen Greiner-Perth It is certified that error appears in the above-identified patent and that said Letters Patent is hereby corrected as shown below:

<u>Title page,</u>
Item [57], ABSTRACT, the abstract should read as follows:

-- ABSTRACT

The invention relates to dispensers for the optionally atomized discharge of an in particular liquid medium from a container. The problem of the invention is to so further develop known dispensers for the discharge of an in particular liquid medium from a container that a one-handed operation is possible ensuring that a discharge of more than one partial charge in a single operation is reliably prevented. In a dispenser according to the invention for the optionally atomized discharge of an in particular liquid medium from a container, the operation of the dispenser takes place in a sequence of manual partial operations of an operating member. During each of the partial operations of the operating member a clearly defined partial charge is discharged from the dispenser. A changeover or reversing operation takes place between two partial operations of the operating member. This changeover operation in each case takes place automatically following the performance of a partial operation. --

The name of the assignee should be corrected to read:

-- [73] Ing. Erich Pfeiffer GmbH, Radolfzell (DE) --

<u>Column 2,</u>
Lines 48-50, should be corrected to read as follows:
-- FIGS. 3a/3b to FIGS. 6a/6b in each case cross-sectional representations and part sectional representation of a second embodiment in which the sleeve is stable with respect to the container during different positions arising during the sequence of partial operations of the dispenser. --

UNITED STATES PATENT AND TRADEMARK OFFICE
CERTIFICATE OF CORRECTION

PATENT NO. : 6,382,465 B1
DATED : May 7, 2002
INVENTOR(S) : Juergen Greiner-Perth It is certified that error appears in the above-identified patent and that said Letters Patent is hereby corrected as shown below:

Column 12,
Line 6, "-the" should be -- the --.

Signed and Sealed this

Twenty-seventh Day of May, 2003

JAMES E. ROGAN
*Director of the United States Patent and Trademark Office*